(12) United States Patent  (10) Patent No.: US 8,808,213 B2
Hendricks  (45) Date of Patent: Aug. 19, 2014

(54) MECHANICALLY ADVANTAGED SPINAL SYSTEM AND METHOD

(75) Inventor: David J. Hendricks, Orlando, FL (US)

(73) Assignee: Hendricks Orthotic Prosthetic Enterprises, Inc., Plano, TX (US)

( * ) Notice: Subject to any disclaimer, the term of this patent is extended or adjusted under 35 U.S.C. 154(b) by 372 days.

(21) Appl. No.: 13/116,687

(22) Filed: May 26, 2011

(65) Prior Publication Data

US 2011/0295169 A1 Dec. 1, 2011

Related U.S. Application Data

(60) Provisional application No. 61/349,247, filed on May 28, 2010.

(51) Int. Cl.
A61B 5/00 (2006.01)

(52) U.S. Cl.
USPC .......................................................... 602/19

(58) Field of Classification Search
CPC ........... A61F 5/02; A61F 5/022; A61F 5/024; A61F 5/028
USPC ............... 128/869, 876; 602/5, 12, 19, 60–61
See application file for complete search history.

(56) References Cited

U.S. PATENT DOCUMENTS

| | | |
|---|---|---|
| 1,184,581 A | 5/1916 | Sigurini |
| 1,577,666 A | 5/1926 | Walter |
| 1,667,989 A | 5/1928 | Rocke |
| 1,727,668 A | 9/1929 | Parkison |
| 2,036,484 A | 4/1936 | LeMay |
| 2,100,964 A | 11/1937 | Kendrick |
| 2,104,699 A | 1/1938 | O'Dell |
| 2,117,309 A | 5/1938 | Fritsch |
| 2,219,475 A | 10/1940 | Flaherty |
| 2,285,612 A | 6/1942 | Rehthaler |
| 2,449,641 A | 9/1948 | Cidissen |
| 2,498,290 A | 2/1950 | Morrison |
| 2,554,337 A | 5/1951 | Lampert |
| 2,733,712 A | 2/1956 | Wuesthoff |
| 2,749,550 A | 6/1956 | Pease |
| 3,052,236 A | 9/1962 | Schrieber |
| 3,096,760 A | 7/1963 | Nelkin |
| 3,097,640 A | 7/1963 | Morgan |
| 3,307,535 A | 3/1967 | Locke |
| 3,434,469 A | 3/1969 | Swift |
| 3,441,027 A | 4/1969 | Lehman |
| 3,452,748 A | 7/1969 | Caprio |

(Continued)

FOREIGN PATENT DOCUMENTS

| | | |
|---|---|---|
| DE | 3613235 A1 | 11/1987 |
| EP | 410904 A1 | 1/1991 |

(Continued)

OTHER PUBLICATIONS

U.S. Appl. No. 12/890,059, filed Sep. 24, 2010, Bledsoe.

*Primary Examiner* — Patricia Bianco
*Assistant Examiner* — Camtu Nguyen
(74) *Attorney, Agent, or Firm* — K&L Gates LLP (57) ABSTRACT

A mechanically advantaged progressive spinal system and method, wherein a string- and pulley-free strap arrangement facilitates adjustment of tension and enhances patient delivered muscle strength, wherein posterior plate curvature may be quickly and easily adjusted to best accommodate a patient's lordosis and kyphosis, and wherein modular components allow for adaptation of mobility and support to improving patient needs.

20 Claims, 11 Drawing Sheets

(56) References Cited

U.S. PATENT DOCUMENTS

| | | |
|---|---|---|
| 3,554,190 A | 1/1971 | Kaplan |
| 3,561,436 A | 2/1971 | Gaylord, Jr. |
| 3,568,670 A | 3/1971 | Gaylord, Jr. |
| 3,570,480 A | 3/1971 | Stubbs |
| 3,578,773 A | 5/1971 | Schultz |
| 3,598,114 A | 8/1971 | Lewis |
| 3,603,316 A | 9/1971 | Lehman |
| 3,623,488 A | 11/1971 | Nakayama |
| 3,717,143 A | 2/1973 | Johnson |
| 3,920,008 A | 11/1975 | Lehman |
| 3,926,183 A | 12/1975 | Spiro |
| 3,927,665 A | 12/1975 | Wax |
| 4,099,524 A | 7/1978 | Cueman et al. |
| 4,135,503 A | 1/1979 | Romano |
| 4,175,553 A | 11/1979 | Rosenberg |
| 4,178,922 A | 12/1979 | Curlee |
| 4,178,923 A | 12/1979 | Curlee |
| 4,245,628 A | 1/1981 | Eichler |
| 4,390,014 A | 6/1983 | Forman |
| 4,459,979 A | 7/1984 | Lewis, Jr. |
| 4,475,543 A | 10/1984 | Brooks et al. |
| 4,508,110 A | 4/1985 | Modglin |
| 4,527,289 A | 7/1985 | Shea |
| 4,545,370 A | 10/1985 | Welsh |
| 4,572,167 A | 2/1986 | Brunswick |
| 4,622,957 A | 11/1986 | Curlee |
| 4,627,109 A | 12/1986 | Carabelli et al. |
| 4,681,113 A | 7/1987 | Coplans |
| 4,721,102 A | 1/1988 | Pethybridge |
| 4,745,911 A | 5/1988 | Bender |
| 4,756,306 A | 7/1988 | Curlee |
| 4,794,916 A | 1/1989 | Porterfield et al. |
| 4,833,730 A | 5/1989 | Nelson |
| 4,836,194 A | 6/1989 | Sebastian et al. |
| 4,964,401 A | 10/1990 | Taigen |
| 4,991,234 A | 2/1991 | Greenberg |
| 4,991,573 A | 2/1991 | Miller |
| 4,992,234 A | 2/1991 | Ohashi et al. |
| 4,993,409 A | 2/1991 | Grim |
| 5,007,412 A | 4/1991 | DeWall |
| 5,036,864 A | 8/1991 | Yewer, Jr. |
| 5,040,524 A | 8/1991 | Votel et al. |
| 5,046,488 A | 9/1991 | Schiek, Sr. |
| 5,062,414 A | 11/1991 | Grim |
| 5,070,866 A | 12/1991 | Alexander et al. |
| 5,072,725 A | 12/1991 | Miller |
| 5,086,758 A | 2/1992 | Schiek, Sr. et al. |
| 5,086,759 A | 2/1992 | Buddingh |
| 5,105,806 A | 4/1992 | Woodhouse et al. |
| 5,111,806 A | 5/1992 | Travis |
| 5,111,807 A | 5/1992 | Spahn et al. |
| 5,122,111 A | 6/1992 | Sebastian et al. |
| 5,147,261 A | 9/1992 | Smith et al. |
| 5,148,549 A | 9/1992 | Sydor |
| 5,176,131 A | 1/1993 | Votel et al. |
| 5,178,163 A | 1/1993 | Yewer, Jr. |
| 5,179,942 A | 1/1993 | Drulias et al. |
| 5,188,585 A | 2/1993 | Peters |
| 5,188,586 A | 2/1993 | Castel et al. |
| 5,195,948 A | 3/1993 | Hill et al. |
| 5,205,814 A | 4/1993 | Lundrigan et al. |
| 5,205,815 A | 4/1993 | Saunders |
| 5,207,635 A | 5/1993 | Richards |
| 5,207,636 A | 5/1993 | Striano |
| 5,226,874 A | 7/1993 | Heinz et al. |
| 5,232,424 A | 8/1993 | Pearson |
| 5,241,704 A | 9/1993 | Sydor |
| 5,257,419 A | 11/1993 | Alexander |
| 5,259,831 A | 11/1993 | LeBron |
| 5,267,947 A | 12/1993 | James |
| 5,302,171 A | 4/1994 | Pearson |
| 5,310,401 A | 5/1994 | Striano |
| 5,316,022 A | 5/1994 | Schiek, Sr. |
| 5,318,505 A | 6/1994 | Sou |
| 5,318,507 A | 6/1994 | Greengarg |
| 5,334,134 A | 8/1994 | Saunders |
| 5,346,461 A | 9/1994 | Heinz et al. |
| 5,351,340 A | 10/1994 | Aldridge |
| 5,363,863 A | 11/1994 | Lelli |
| 5,387,183 A | 2/1995 | Jones |
| 5,388,273 A | 2/1995 | Sydor et al. |
| 5,388,274 A | 2/1995 | Glover et al. |
| 5,396,906 A | 3/1995 | Harrold |
| 5,399,150 A | 3/1995 | Saunders |
| 5,399,151 A | 3/1995 | Smith |
| 5,421,809 A | 6/1995 | Rise |
| 5,426,791 A | 6/1995 | Sydor et al. |
| 5,429,587 A | 7/1995 | Gates |
| 5,432,951 A | 7/1995 | Yewer, Jr. |
| 5,433,697 A | 7/1995 | Cox |
| 5,437,615 A | 8/1995 | Pekar et al. |
| 5,437,617 A | 8/1995 | Heinz et al. |
| 5,445,601 A | 8/1995 | Harlow |
| 5,447,498 A | 9/1995 | Watson |
| 5,450,627 A | 9/1995 | Grilliot |
| 5,450,858 A | 9/1995 | Zablotsky et al. |
| 5,470,000 A | 11/1995 | Munoz |
| 5,484,395 A | 1/1996 | DeRoche |
| 5,489,260 A | 2/1996 | Striano |
| 5,499,965 A | 3/1996 | Sanchez |
| 5,500,959 A | 3/1996 | Yewer, Jr. |
| 5,503,620 A | 4/1996 | Danzger |
| 5,533,961 A | 7/1996 | Iwata |
| 5,536,246 A | 7/1996 | Saunders |
| 5,547,462 A | 8/1996 | Lanigan et al. |
| 5,548,843 A | 8/1996 | Chase et al. |
| 5,551,085 A | 9/1996 | Leighton |
| 5,560,046 A | 10/1996 | Iwamasa et al. |
| 5,581,810 A | 12/1996 | Yewer, Jr. |
| 5,586,969 A | 12/1996 | Yewer, Jr. |
| 5,591,122 A | 1/1997 | Yewer, Jr. |
| 5,598,583 A | 2/1997 | Victor |
| 5,599,287 A | 2/1997 | Beczak, Sr. et al. |
| 5,611,084 A | 3/1997 | Garry et al. |
| 5,628,721 A | 5/1997 | Arnold et al. |
| 5,634,891 A | 6/1997 | Beczak, Sr. et al. |
| 5,651,763 A | 7/1997 | Gates |
| 5,656,020 A | 8/1997 | Greengarg |
| 5,656,021 A | 8/1997 | Greengarg |
| 5,690,122 A | 11/1997 | Weber-Unger |
| 5,690,609 A | 11/1997 | Heinze, III |
| 5,693,006 A | 12/1997 | Slautterback |
| 5,722,940 A | 3/1998 | Gaylord, Jr. et al. |
| 5,728,055 A | 3/1998 | Sebastian |
| 5,762,619 A | 6/1998 | Simon |
| 5,765,224 A | 6/1998 | Johnson |
| 5,776,087 A | 7/1998 | Nelson et al. |
| 5,782,782 A | 7/1998 | Miller |
| 5,785,671 A | 7/1998 | Striano |
| 5,785,672 A | 7/1998 | Mattison et al. |
| RE35,940 E | 10/1998 | Heinz et al. |
| 5,820,575 A | 10/1998 | Cabrera et al. |
| 5,833,638 A | 11/1998 | Nelson |
| 5,853,378 A | 12/1998 | Modglin |
| 5,865,774 A | 2/1999 | Brenman et al. |
| 5,934,599 A | 8/1999 | Hammerslag |
| 5,967,998 A | 10/1999 | Modglin |
| 5,984,885 A | 11/1999 | Gaylord, Jr. et al. |
| 5,984,886 A | 11/1999 | Miller |
| 6,053,883 A | 4/2000 | Schiek, Sr. |
| 6,068,606 A | 5/2000 | Castel et al. |
| 6,080,121 A | 6/2000 | Madow et al. |
| 6,099,490 A | 8/2000 | Turtzo |
| 6,137,675 A | 10/2000 | Perkins |
| 6,146,345 A | 11/2000 | Mignard |
| 6,156,001 A | 12/2000 | Frangi et al. |
| 6,165,147 A | 12/2000 | Morrow |
| 6,190,343 B1 | 2/2001 | Heinz et al. |
| 6,213,968 B1 | 4/2001 | Heinz et al. |
| 6,289,558 B1 | 9/2001 | Hammerslag |
| 6,319,217 B1 | 11/2001 | Darcey |
| 6,322,529 B1 | 11/2001 | Chung |
| 6,336,908 B1 | 1/2002 | Slautterback |
| 6,342,044 B1 | 1/2002 | Frangi et al. |

(56) References Cited

U.S. PATENT DOCUMENTS

| | | |
|---|---|---|
| 6,419,652 B1 | 7/2002 | Slautterback |
| 6,478,759 B1 | 11/2002 | Modglin et al. |
| 6,500,137 B1 | 12/2002 | Molino et al. |
| 6,503,215 B1 | 1/2003 | Reinhardt et al. |
| 6,517,502 B2 | 2/2003 | Heyman et al. |
| 6,524,264 B1 | 2/2003 | Hutchinson |
| 6,533,740 B2 | 3/2003 | Reinecke et al. |
| 6,602,214 B2 | 8/2003 | Heinz et al. |
| 6,609,642 B2 | 8/2003 | Heinz et al. |
| 6,610,022 B1 | 8/2003 | Ashbaugh et al. |
| 6,635,025 B1 | 10/2003 | Reinecke et al. |
| 6,666,838 B2 | 12/2003 | Modglin et al. |
| 6,689,082 B2 | 2/2004 | Reinecke et al. |
| 6,702,770 B2 | 3/2004 | Bremer et al. |
| 6,702,771 B1 | 3/2004 | Reinecke et al. |
| 6,746,413 B2 | 6/2004 | Reinecke et al. |
| 6,755,799 B2 | 6/2004 | Toda |
| 6,766,532 B1 | 7/2004 | Cabana |
| 6,776,767 B2 | 8/2004 | Reinecke et al. |
| 6,840,916 B2 | 1/2005 | Kozersky |
| 6,896,662 B2 | 5/2005 | Heffez |
| 6,921,375 B2 | 7/2005 | Kihara |
| 6,923,779 B1 | 8/2005 | Choiniere |
| 6,932,780 B2 | 8/2005 | Kozersky |
| 6,951,547 B1 | 10/2005 | Park et al. |
| 6,962,572 B1 | 11/2005 | Zahiri |
| 6,964,644 B1 | 11/2005 | Garth |
| 6,974,432 B2 | 12/2005 | Reinecke et al. |
| 6,997,892 B2 | 2/2006 | Reinecke |
| 7,001,350 B2 | 2/2006 | Grosso |
| 7,001,351 B2 | 2/2006 | Reinecke et al. |
| 7,025,737 B2 | 4/2006 | Modglin |
| 7,037,284 B2 | 5/2006 | Lee |
| 7,070,572 B2 | 7/2006 | Reinecke et al. |
| 7,074,201 B2 | 7/2006 | Reinecke et al. |
| 7,077,794 B1 | 7/2006 | Bray |
| 7,083,585 B2 | 8/2006 | Latham |
| 7,101,348 B2 | 9/2006 | Garth et al. |
| 7,118,543 B2 | 10/2006 | Telles et al. |
| 7,160,262 B2 | 1/2007 | Wicks |
| 7,186,229 B2 | 3/2007 | Schwenn et al. |
| 7,201,727 B2 | 4/2007 | Schwenn et al. |
| 7,276,038 B2 | 10/2007 | Reinecke et al. |
| 7,306,571 B2 | 12/2007 | Schwenn et al. |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,322,952 B2 | 1/2008 | Chase et al. |
| 7,329,231 B2 | 2/2008 | Frank |
| 7,364,558 B2 | 4/2008 | Weaver, II et al. |
| 7,371,222 B2 | 5/2008 | Heinz et al. |
| 7,449,005 B2 | 11/2008 | Pickering et al. |
| 2001/0008955 A1 | 7/2001 | Garth |
| 2001/0020144 A1 | 9/2001 | Heinz et al. |
| 2002/0068890 A1 | 6/2002 | Schwenn et al. |
| 2002/0123705 A1 | 9/2002 | Reinecke et al. |
| 2002/0193720 A1 | 12/2002 | Reinecke et al. |
| 2003/0050585 A1 | 3/2003 | Modglin |
| 2003/0097085 A1 | 5/2003 | Reinecke et al. |
| 2004/0167449 A1 | 8/2004 | Heffez et al. |
| 2004/0220502 A1 | 11/2004 | Arden |
| 2005/0015034 A1 | 1/2005 | Sansone et al. |
| 2005/0043660 A1 | 2/2005 | Stark et al. |
| 2005/0267390 A1 | 12/2005 | Garth et al. |
| 2006/0129077 A1 | 6/2006 | Parizot |
| 2006/0282032 A1 | 12/2006 | Smith et al. |
| 2007/0073204 A1 | 3/2007 | Suarez et al. |
| 2007/0156073 A1 | 7/2007 | Smith |
| 2007/0197943 A1 | 8/2007 | Hakonson et al. |
| 2008/0004557 A1 | 1/2008 | Wolanske |
| 2008/0045873 A1 | 2/2008 | Zours |
| 2008/0171955 A1 | 7/2008 | Jaccard |

FOREIGN PATENT DOCUMENTS

| | | |
|---|---|---|
| EP | 459082 A1 | 12/1991 |
| FR | 2569344 A1 | 2/1986 |
| GB | 2120100 A | 11/1983 |
| JP | 6078943 A | 3/1994 |
| WO | WO0905502 | 5/1990 |
| WO | WO9318724 A1 | 9/1993 |
| WO | WO9412125 A1 | 6/1994 |
| WO | WO9965428 | 12/1999 |
| WO | WO2008037584 | 4/2008 |

MECHANICALLY ADVANTAGED SPINAL SYSTEM AND METHOD

PRIORITY CLAIM

This application claims priority to and the benefit of provisional U.S. Patent Application Ser. No. 61/349,247, filed May 28, 2010, entitled, "Mechanically Advantaged Spinal System", the entire contents of which are incorporated herein by reference and relied upon.

BACKGROUND

The present disclosure relates generally to spinal orthoses, and more particularly, to a mechanically advantaged spinal system, which may be a progressive spinal system. Spinal orthoses are frequently prescribed and worn to limit body motion, to reduce body-realized load, and/or to improve body function, essentially according to accomplishment of the same purpose: 1) compression of the abdomen, 2) limitation of spinal motion, and 3) protection of the torso. Indications of use may include, without limitation, osteoporosis, spondylolysis, burst fracture, spinal stenosis, spondylolisthesis, chronic back pain, degenerative disc disease, herniated or bulging disc, ligament strain/sprain, compression fracture, spinal stabilization, post-laminectomy, or the like. Irrespective of the indication, however, orthosis design necessarily dictates functionality and overall performance.

Typically, orthosis attributes and features are selectively balanced according to the needs of a particular patient, wherein consideration may be given to such features as the overall weight and adjustability of the orthosis, including its ability to accommodate patient size variation, the ease of donning (putting on) and doffing (taking off), the overall functionality and cosmesis (desirable physical appearance), and, as with essentially any medical tool or device, durability of materials and cost. Unfortunately, in spinal bracing, one benefit or attribute must typically be traded to get another, e.g. comfort versus support, rigid control versus softness, and/or custom-like fit versus simplicity.

Functionality and performance are obviously critical considerations; however, the patient must be able to properly and effectively don the device in order for the functionality and performance to be realized. Moreover, patients must be encouraged to regular wear. Mechanically advantaged devices have been introduced to assist in a patient's ability to put on and wear an orthosis, with proper force delivered thereby. Strings and cords that serve to tighten these devices are tensively woven about pulleys or posts. The strings are typically connected to a plurality of pull tabs that a patient must pull bi-directionally away from the body, looped about his or her thumbs. These devices may be effective, but the tightening movement necessary may be outside the range of movement for at least some patients. Moreover, the narrow strings or cords may disadvantageously tangle, fray or jam, and at least some such devices require very particular positioning after patient doffing in order to allow for re-donning with functionality of the tightening system to be retained. And, the added weight and construction complexity of the pulleys or posts, generally installed inside enclosed pockets during manufacture, may impact comfort of wear and cost.

Cost of treatment is frequently an important consideration, first in the initial prescription and purchase, and thereafter during the course of the healing process. That is, over the treatment period, as a patient heals, the necessary level of support and control typically changes. In order to accommodate the changing needs, purchase of one or more additional orthoses may be disadvantageously necessary. Customization of posterior plates' lordosis and kyphosisspecifications, as well, may be disadvantageously prohibitive, wherein a patient is generally relegated to selection of closest general-fit options to his or her needs.

Therefore, it is readily apparent that there is a need for a spinal orthosis system, wherein a comfortable, supportive and cost-effective treatment is enabled, with custom-like fit, mechanically advantaged and easily adjustable force delivery, adaptability to patient healing and progression of needs, simplicity and durability of design, and ease and encouragement of patient use, thereby avoiding the above-discussed disadvantages.

SUMMARY

Briefly described, in one embodiment, the present apparatus and method overcomes the above-mentioned disadvantages and meets the recognized need for such a device by providing a mechanically advantaged progressive spinal system, wherein a string- and pulley-free strap arrangement facilitates adjustment of tension and enhances patient delivered muscle strength, wherein posterior plate curvature may be quickly and easily adjusted to best accommodate a patient's lordosis and kyphosis, and wherein modular components allow for adaptation of mobility and support to improving patient needs.

According to its major aspects and broadly stated, the present device is a mechanically advantaged progressive spinal system with modular brace components ranging from an orthopedic belt to a full sagittal-coronal control orthosis, wherein a foundational element is tensively adjusted with a single, unidirectional pull and resulting force delivery from straps rerouted 3:1 and 2:1 for a 6× mechanical advantage, and wherein select posterior plate angles are adjusted with a simple joint and strap feature.

More specifically, the system of the present disclosure can comprise a mechanically advantaged belt and a plurality of plates and shells, functioning as a system of orthotic braces capable of progressively diminishing support and control, and increasing mobility, adapting to patient improvement. Each of the braces of the system serves to compress the abdomen, limit spinal motion, and protect the torso, but they range in height and stiffness to allow for proper support according to the necessary circumstances of patient status. Additionally, the mechanically advantaged belt has two selectable profiles, and may be circumferentially reduced and/or expanded, according to patient size and preference.

According to one embodiment, the belt structure has two general support members of breathable mesh, with a soft patient interface. Each general support member has a plurality of internal structural support elements provided in a spaced-apart configuration; each has an outer surface substantially covered with hook and pile fastener; and each has a pair of straps fixed proximate the inner posterior surface thereof for selective attachment of a posterior plate. The inner anterior surface of one of the two general support members has an accessible pocket, wherein an anterior plate may be selectively carried therewithin. The inner anterior surface of the other of the two general support members has hook and pile fastener complementary to that of the outer surface provided thereon, whereby the two general support members may be removably secured together proximate the front of the body of the patient.

The posterior belt closure mechanism has two closure support members, each removably carried on the outer surface of the outer posterior surface of a respective one of the two general support members. One of the closure support members has the ends of an elongate closure strap affixed thereto, and has two support rings positioned therebetween. The other of the closure support members also has two support rings positioned thereon, wherein the elongate closure strap extends from each of the affixed points on the first closure support member through the support rings of the other closure support member, and back through the support rings of the first closure support member, whereafter the elongate closure strap is looped through a strap connector element. A D-ring cinching strap is affixed to one of the general support members of the belt, serving to activate the 6× mechanical advantage of the closure mechanism, wherein patient muscular pulling force delivered thereto causes slidable movement of the strap connector element there along, thereby delivering a pulling force on the elongate closure strap, tightening the belt, with inverse handling steps for loosening.

According to the needs of the patient, one or more of a plurality of selectable features may be added. For example, an extender may be attached, wherein the anterior plate is pre-drilled to facilitate acceptance thereof. An optional belt panel also may be added to enable accommodation of sizes up to and including 5×. Additionally, in order to facilitate progressive adaptation, pluralities of posterior configurations are possible for use with the mechanically advantaged belt. A first posterior configuration is tailored for aggressive support, with a molded and padded posterior shell adapted with belt retainer straps and a central spinal relief zone. This posterior configuration is also adapted for use with a taller thoracolumbosacral orthosis (TLSO).

Another posterior configuration is used for a standard chairback brace or lumbosacral orthosis (LSO), wherein firm support is enabled by a padded posterior plate with adjustable lordosis and kyphosis straps and belt retainer straps. Yet another available posterior configuration is used for a mid-lumbosacral orthosis (mid-LSO), wherein moderate support is enabled by a padded posterior plate with an adjustable lordosis strap and belt retainer straps. The posterior plates with adjustable lordosis and/or kyphosis are configured as sturdy structures with bend-accommodating regions and adjustable straps related thereto. Each plate may be selectively bent relative to its bend-accommodating region(s), wherein the related adjustable strap may be tightened to enable maintenance of the selected bend during wear of the orthosis.

Thus, a feature and advantage of the present system is its ability to perform a cost-effective orthosis, suitable for utilization throughout an entire treatment period, wherein, for example, a four stage progressive brace system may be followed, with a first stage configuration having a rigid posterior shell deployed with the mechanically advantaged belt having a rigid anterior plate therein, a second stage configuration having a semi-rigid posterior plate and a rigid anterior plate, a third stage having a rigid anterior plate but no posterior plate, and a fourth stage having no anterior or posterior plate.

Another feature and advantage of the present system is its ability to allow for custom-like lumbar lordosis and/or kyphosis fit, without heating or remolding.

Another feature and advantage of the present system is its ability to perform as a mechanically advantaged device operated with one hand.

Yet another feature and advantage of the present system is its ability to deliver at least a 6:1 mechanical advantage.

Still another feature and advantage of the present system is its ability to eliminate risk of tangling, jamming, tearing and/or fraying relative to strings or cords.

Yet still another feature and advantage of the present system is its ability for easy and effective donning and doffing, without necessitating complex stretching or arrangement after doffing and/or prior to donning.

Still yet another feature, and advantage of the present system is its ability to be cost-effectively manufactured.

Yet another feature and advantage of the present system is its ability to tensively adjust without the need for pulleys or posts.

Still another feature and advantage of the present system is its ability to conform to a patient's body with one easy pull.

Yet another feature and advantage of the present system is its ability to enable progressive increase of mobility and decrease of support as a patient improves.

Still yet another feature and advantage of the present system is its ability to be easily disassembled and cleaned.

Another feature and advantage of the present system is that it is MRI compatible.

These and other features and advantages of the invention will become more apparent to one skilled in the art from the following description and claims when read in light of the accompanying drawings.

BRIEF DESCRIPTION OF THE FIGURES

The present disclosure will be better understood by reading the Detailed Description of the Preferred and Alternate Embodiments with reference to the accompanying drawing figures, in which like reference numerals denote similar structure and refer to like elements throughout, and in which.

DETAILED DESCRIPTION OF THE PREFERRED AND ALTERNATE EMBODIMENTS

In describing the preferred and alternate embodiments of the present disclosure, as illustrated in the figures and/or described herein, specific terminology is employed for the sake of clarity. The disclosure, however, is not intended to be limited to the specific terminology so selected, and it is to be understood that each specific element includes all technical equivalents that operate in a similar manner to accomplish similar functions.

Referring now to FIGS. 1 to 9A and 9B, mechanically advantaged progressive spinal system 10 is defined by plurality of modular brace components 12, preferably comprising a plurality of plates and (referred to herein generally and collectively as plates or shells 20) and mechanically advantaged belt 80. Belt 80 has preferred closure mechanism 82, wherein 6× mechanical advantage is realized thereby. Closure mechanism 82 in the illustrated embodiment is a strap or member in looped communication with support members or wings 88a and 88b.

Figure 3A:
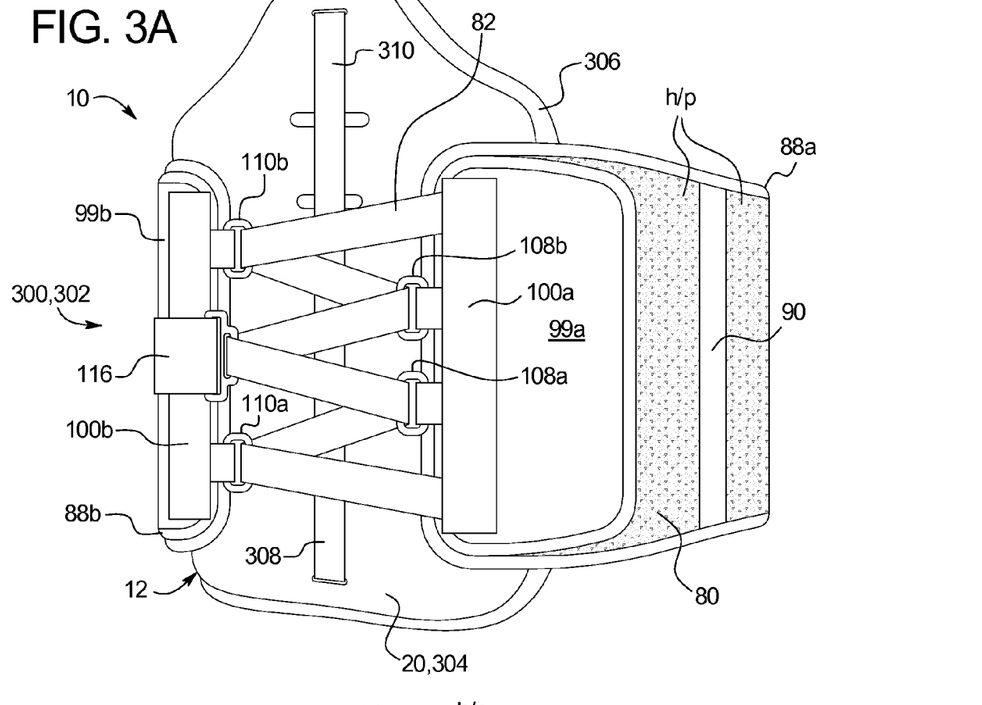
FIG. 3A is a perspective view of a second brace configuration, constructed and arranged to provide an intermediate amount of bracing force.
Figure 3B:
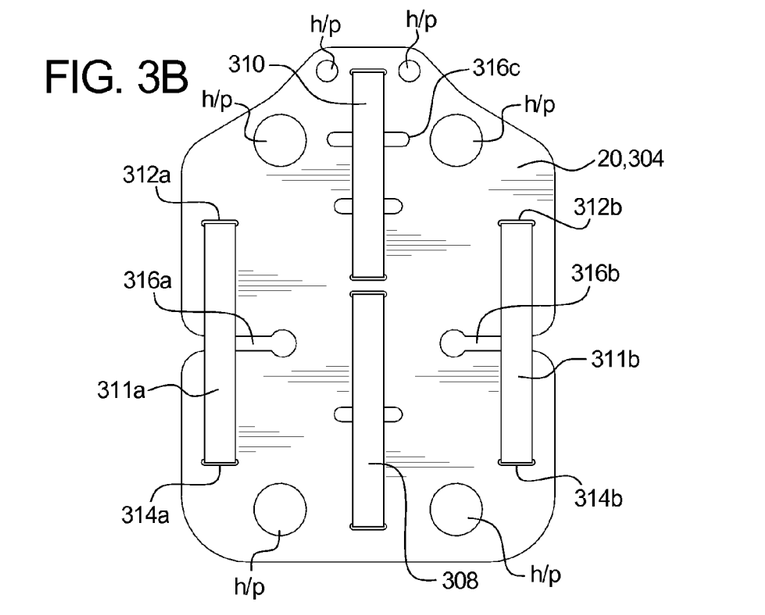
FIG. 3B is a plan view of an inner surface of a posterior plate for the brace configuration shown in FIG. 3A.
Figure 4A:
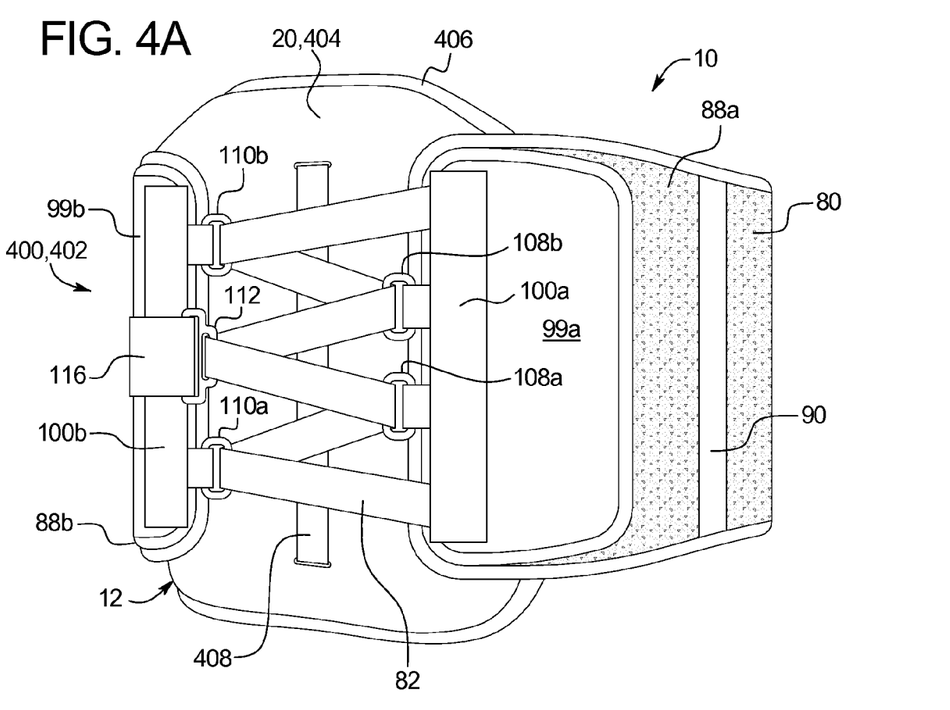
FIG. 4A is a perspective view of a third brace configuration, constructed and arranged to provide a moderate amount of bracing force.
Figure 4B:
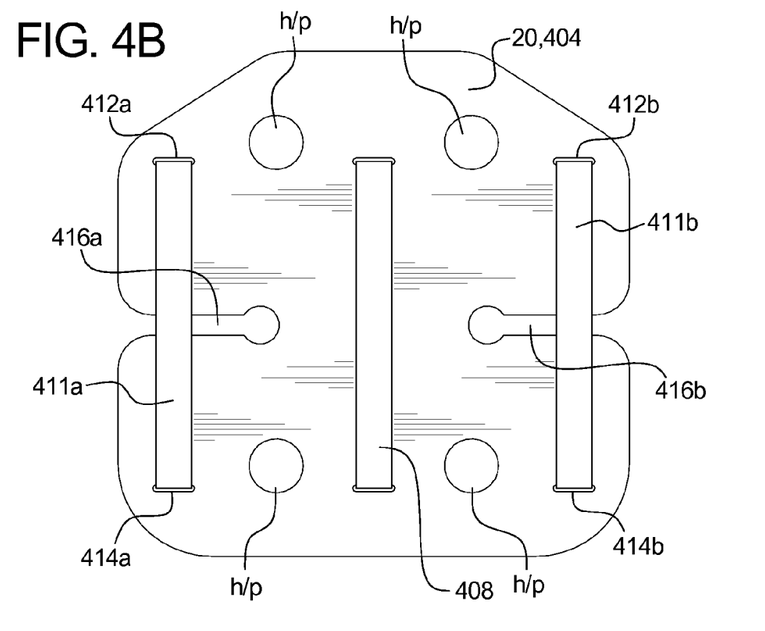
FIG. 4B is a plan view of an inner surface of a posterior plate for the brace configuration shown in FIG. 4A.
Figure 5A:
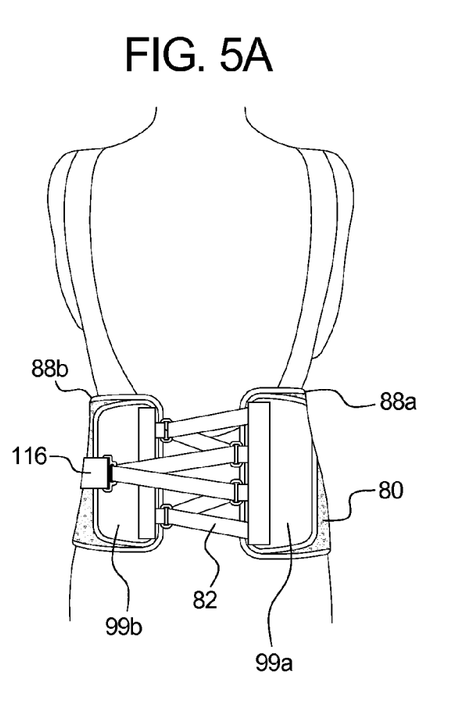
FIG. 5A is a rear view of one embodiment of a mechanically advantaged belt of the present disclosure as worn on a patient.
Figure 5B:
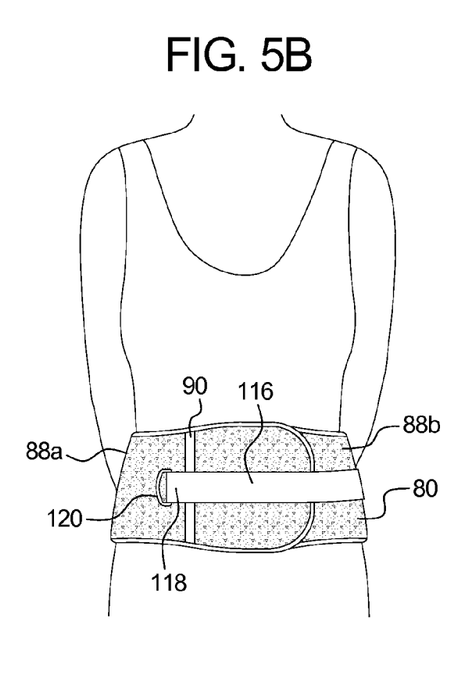
FIG. 5B is a front view of one embodiment of a mechanically advantaged belt of the present disclosure as worn on a patient.
Figure 5C:
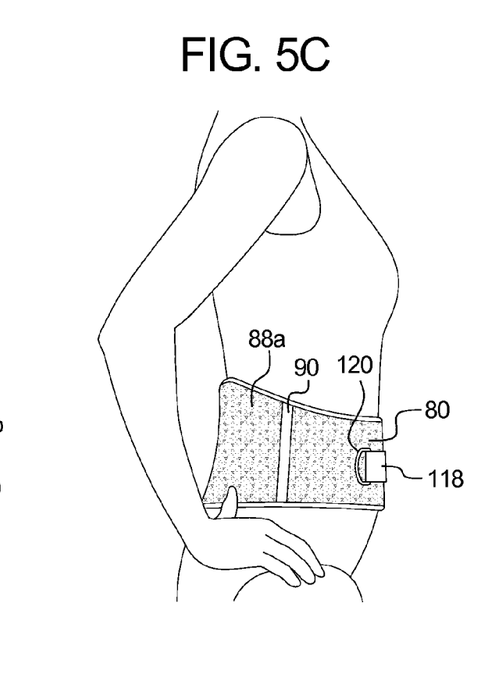
FIG. 5C is a side view of one embodiment of a mechanically advantaged belt of the present disclosure as worn on a patient.

Belt 80 is designed and intended for independent use as an orthopedic belt, such as depicted in FIGS. 5A to 5C, and is also designed and intended for use in combination with one or more of the plurality of plates and shells 20, such as depicted in FIGS. 2A, 2B, 3A, 3B, 4A and 4B. In such manner, mechanically advantaged progressive spinal system 10 may accommodate changing patient needs during a single course of treatment. Belt 80 in one embodiment has dimensions relatively standard for orthopedic belts, with standard belt 84 (FIG. 6A) having a front height ranging for example from six-and-one-half (6.5) to eight (8) inches, a waist circumference of for example from twenty-eight (28) to seventy-three (73) inches, and a back height of ten-and-one-half (10½) inches in one embodiment. It should be noted that other dimensions could be used without departing from the intended scope of the device. One such example is offered by low profile belt 86 (FIG. 1), with a front height of 6 inches to 6.5 inches. Another example may be found in component readjustment of belt 80, wherein waist circumference measurements may be reduced thereby, as will be discussed further herein. Still another example, yet without limitation, is provided by optional belt panel (not illustrated), wherein waist sizes up to 5× may be accommodated therewith.

Figure 1:
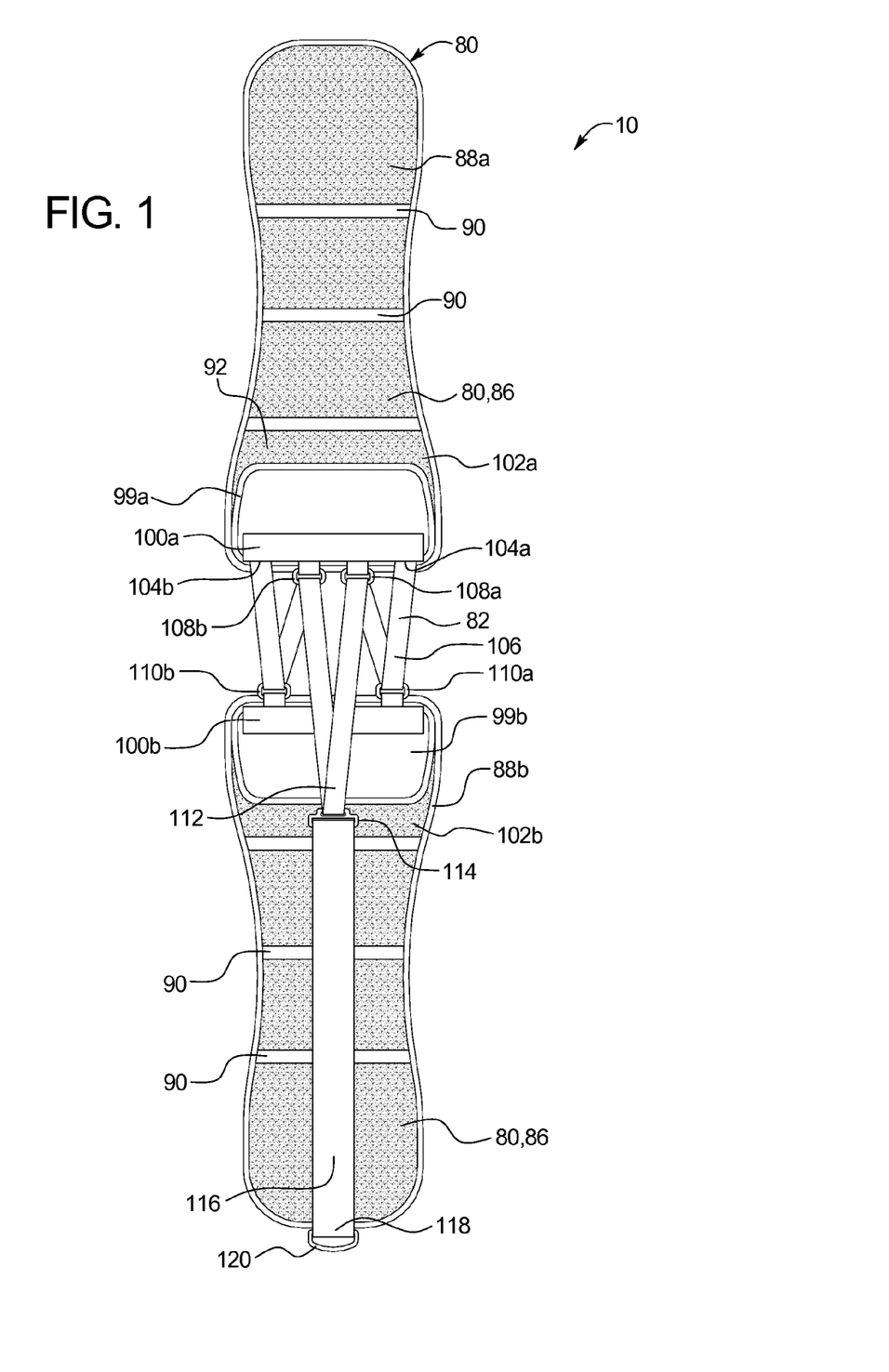
FIG. 1 is a plan view of one embodiment of a mechanically advantaged belt of the present disclosure.

According to one embodiment, belt 80 has two general support members 88a and 88b, represented in FIG. 1, each manufactured in one embodiment of breathable mesh and with a soft patient interface, and generally forming a "wing" of belt 80. Each general support member or wing 88a, 88b can be provided with a plurality of internal structural support elements 90, for example, in a spaced-apart configuration. Each of the plurality of internal structural support elements 90 is in one embodiment a generally flat and rectangular shaped stay, with a sturdy construction, wherein any suitably performing material and/or shape, e.g., rigid plastic or metal, may be used to accomplish the supportive purpose thereof. Outer surface 92 of each general support member or wing 88a, 88b is at least substantially covered with hook and pile fastener materials. In such manner, outer surface 92 of each general support member 88a, 88b is adapted to receive and retain appropriately complementary accessories thereon, in essentially any position. Each general support member 88a, 88b can further include pair of plate attachment straps 94, as may be representatively seen in FIGS. 9A and 9B, which are fixedly positioned at the inner posterior surface of belt 80 in one embodiment. Nevertheless, other means for plate securement could alternately be used, and belt 80 could even have one of a plurality of plates and shells 20 permanently affixed thereto, although such adaptation would essentially eliminate the beneficially accommodating nature of preferred system 10.

General support members 88a and 88b have differing attributes in various embodiments. For example, inner anterior surface 98b of general support member 88b can be provided with accessible pocket (FIGS. 6A ands 9A), wherein an anterior plate (not illustrated) may be selectively carried therewithin for maximized frontal support. In the illustrated embodiment of FIG. 9A, pocket 98b allows the anterior plate to slide removably in from the top, after which flaps 96a and 96b, e.g., having hook material underneath, hingedly close onto the inner pocket surface, e.g., having pile material, to hold the anterior plate in place.

Inner anterior surface 98a of general support member 88a (FIGS. 6A, 6B and 9B) can have hook material complementary to the pile material of outer surface 92 (FIG. 1) provided thereon, whereby general support member 88a may be securely positioned proximate outer surface 92 of general support member 88b in order that general support members 88a and 88b may be removably secured together proximate the front of the body of the patient. It should be noted that although hook and pile fastening is one preferred mode of fastening, other manners of fastening may alternately be used, such as, for exemplary purposes only, snaps, hooks and eyes, clips, or the like.

As illustrated best in FIGS. 1, 2A, 3A and 4A, closure mechanism 82 has two closure support members 99a, 99b, each removably carried (e.g., hook and pile attachment) on outer surface 92 of respective outer posterior surfaces 102a, 102b of general support members 88a, 88b. In the illustrated embodiment, closure support member 99a holds ends 104a, 104b of elongate closure strap 106 affixed thereto, and has two support rings 108a, 108b positioned between ends 104a, 104b. Closure support member 99b as illustrated in FIG. 1 also has two support rings 110a, 110b positioned thereon, wherein elongate closure strap 106 also (i) extends from affixed end 104a on closure support member 99a, (ii) through support ring 110a on closure support member 99b, and (iii) back to and through support ring 108a on closure support member 99a, and wherein elongate closure strap 106 also (i) extends from affixed end 104b on closure support member 99a, (ii) through supporting ring 110b on closure support member 99b, and (iii) back to and through supporting ring 108b on closure support member 99a. In such manner, elongate closure strap 106 is formed in a closed loop arrangement, with loop end 112 of strap 106 engaged with loose strap connector element 114.

In the illustrated embodiment, closure support members 99a, 99b are provided with, e.g., metal or hard plastic, stiffening stays 100a, 100b, respectively, which can be removably attached to support members 99a, 99b, e.g., via hook and pile attachment. It is anticipated that closure support members 99a, 99b could alternatively be permanently affixed to belt 80, or could be integrally formed therewith, although the illustrated removable configuration facilitates maximum adjustability for belt 80 and system 10.

A cinching strap 116 is carried by general support member 88b, wherein a first end of cinching strap 116 (folded under itself at loop end 112 as viewed in FIG. 1) is affixed to outer surface 92 of general support member 88b, wherein strap connector element 114 is slidably carried by cinching strap 116, and wherein second end 118 of cinching strap 116 carries D-ring 120 in the embodiment illustrated in FIG. 1. Inner surface (not illustrated) of cinching strap 116 has in one embodiment a hook and pile fastener h/p provided thereon (FIGS. 6D and 9A), proximate second end 118 thereof. As will be further discussed, a patient can grasp D-ring 120 and/or cinching strap 116, delivering a pulling force thereto, in order to activate the 6× mechanical advantage of closure mechanism 82, wherein patient muscular pulling force delivered to cinching strap 116 causes slidable movement of strap connector element 114 along cinching strap 116, thereby delivering a pulling force to elongate closure strap 106 and tightening belt 80, whereafter hook and pile fastener engagement of inner surface of second end 118 of cinching strap 116 may be accomplished at essentially any position on outer surface 92 of general support elements 88a or 88b. It is noted that cinching strap 116 could be provided without D-ring 120, wherein, for example, a simple strap loop (not illustrated) could be defined at second end 118 thereof, or some other structural addition to facilitate grasping.

Figure 6A:
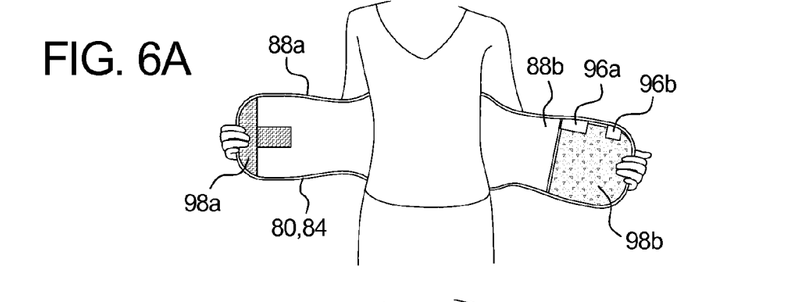
FIGS. 6A to 6E illustrate a series of one embodiment of the belt of the present disclosure being donned.
Figure 6B:
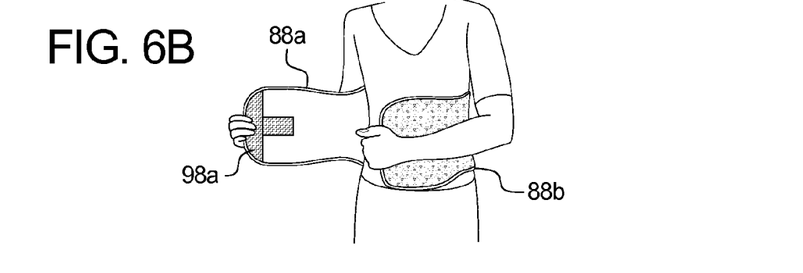
Figure 6C:
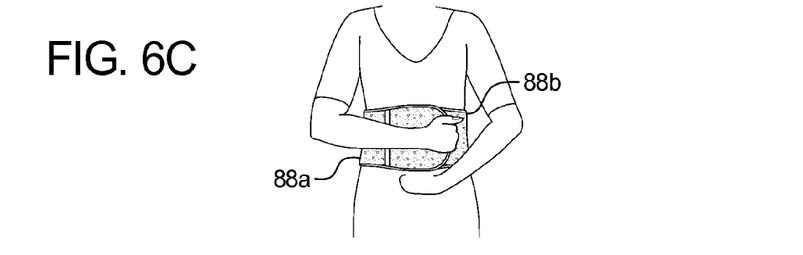
Figure 6D:
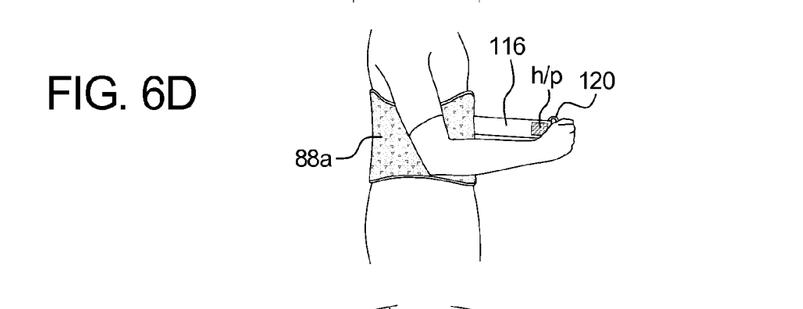
Figure 6E:
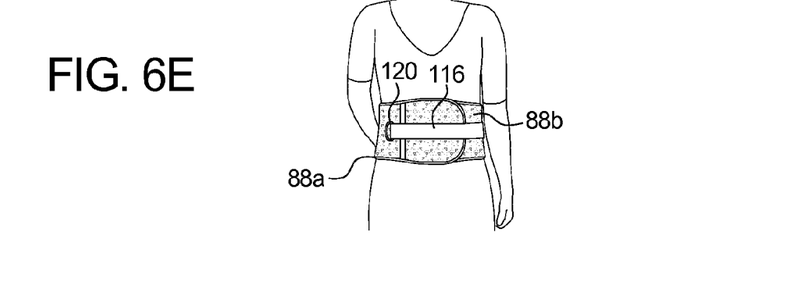

The series presented in FIGS. 6A to 6E shows one set of steps for donning system 10. In a first step as shown in FIG. 6A, a patient places and centers belt 80 behind his/her body on his/her back, with one hand gripping each end of belt 80. In the step of FIG. 6B, the patient brings general support member or wing 88b around to the front of his/her body, against the abdomen, and in the step of FIG. 6C, brings general support member or wing 88a also around to the front of his/her body (e.g., with hook material), securing inner anterior surface 98a of general support member or wing 88a to the outer surface (e.g., with pile material) of general support member or wing 88b. Thereafter, in the step of FIG. 6D, the patient grasps D-ring 120, or second end 118 of cinching strap 116 directly, and pulls, activating closure mechanism 82 and delivering mechanically advantaged tightening to belt 80. In FIG. 6E, the user removably attaches the hook and pile fastening member h/p (illustrated in FIG. 6D) located on the inside of strap 116 to the outer (e.g., pile) material of support member or wing 88a. The simple, single-pull action squeezes system 10 to essentially conform to the shape of the patient's torso. Further, quick and easy variation of tension is accomplished, such as for tightening during a more strenuous task and loosening during rest and relaxation period, with one simple motion.

As previously noted, according to the needs of the patient, system 10 can add one or more of a plurality of selectable features. For example, an extender (not illustrated) may be attached, wherein an anterior plate (not illustrated), carried in accessible pocket 98b is in one embodiment pre-drilled to facilitate acceptance thereof. An extender is a product that extends the coverage area of the brace. The extender can attach to the anterior panel via plural, e.g., four, screws to extend support up to the patient's sternal notch. System 10 can accommodate different types of extenders with different patient interfaces (e.g., pivoting, single pad, dual pads, etc.). Additionally, to enable accommodation of sizes through 5×, an extender panel (not illustrated) may be selectively incorporated.

Figure 2A:
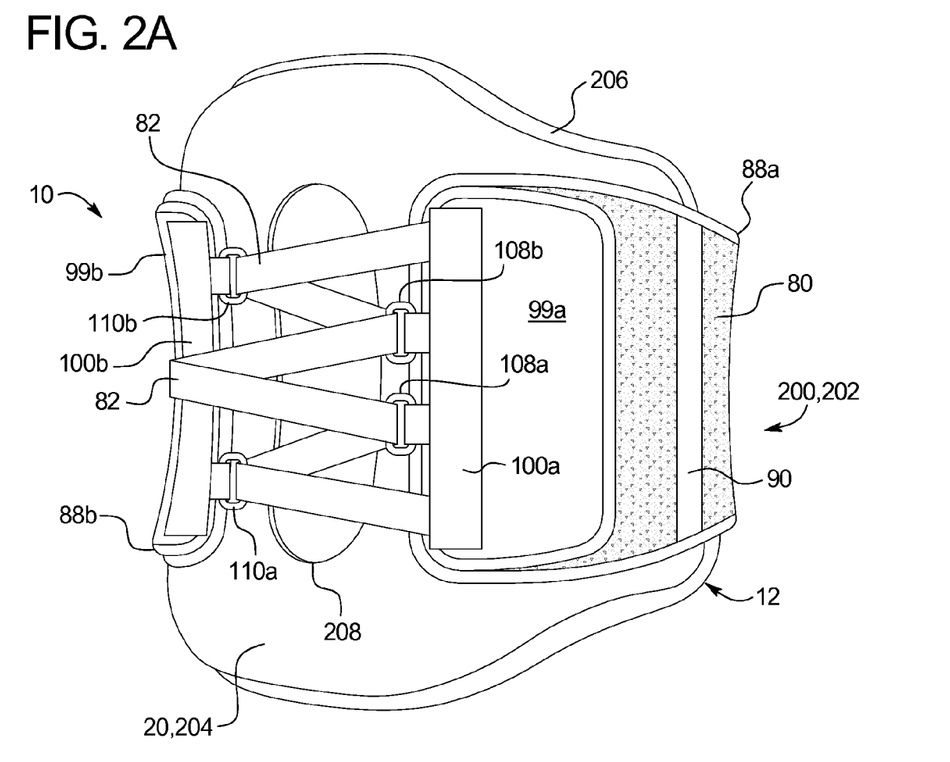
FIG. 2A is a perspective view of a first brace configuration, constructed and arranged to provide and aggressive amount of bracing force.
Figure 2B:
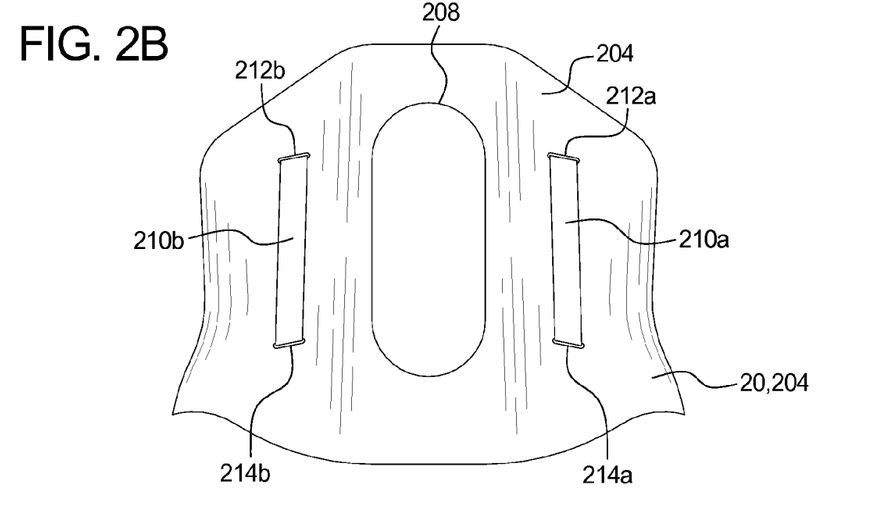
FIG. 2B is a plan view of an outside of a posterior plate for the brace configuration shown in FIG. 2A.

Moreover, and beneficially, in order to facilitate progressive adaptation to patient needs, a plurality of posterior configurations are possible for use with mechanically advantaged belt 80, wherein mechanically advantaged progressive spinal system 10 includes a plurality of plates and shells 20, further described individually as posterior shells 204, 304, and 404 (plates and shells 20 referring collectively or generally to shells 204, 304 and 404), wherein use in progressive series can dynamically accommodate most courses of treatment. First posterior configuration 200 is representatively depicted' in FIG. 2A, as thoracolumbosacral orthosis (TLSO) 202, tailored for aggressive support or bracing force. TLSO 202 includes a posterior shell 204, wherein posterior shell 204 in one embodiment is of a molded construction, e.g., of KYDEX or a similar sturdy, lightweight, and easily cleanable material, and is adapted with interior padding 206, such as a plush, tri-laminate pad, as well as central spinal relief zone, or aperture, 208, for maximized patient comfort. As illustrated in FIGS. 2A and 2B, shell 204 is pre-formed or pre-bent to provide the aggressive support or bracing force. In one embodiment, interior padding 206 is removably secured to posterior shell 204 via hook and pile fastener.

Figure 9A:
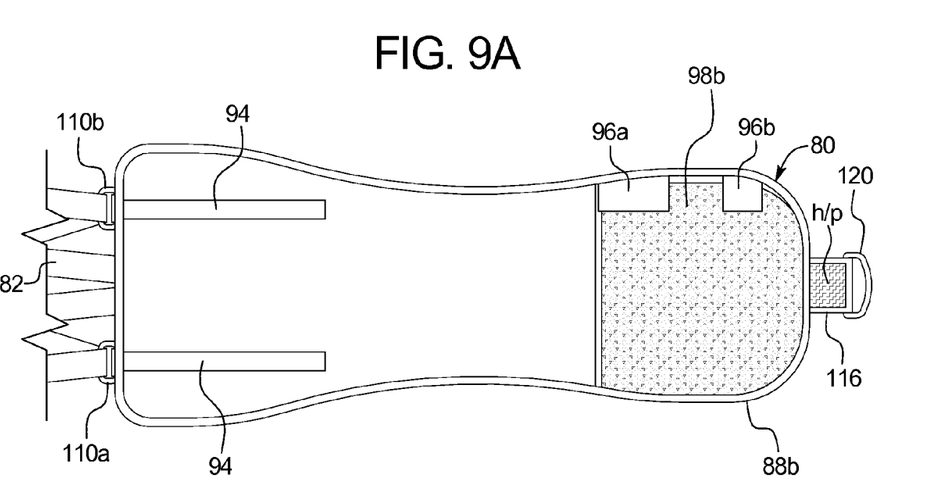
FIGS. 9A and 9B illustrate interior sides of one embodiment of the belt's general support members or wings of the present disclosure having straps for selectively receiving one of the shells of the present disclosure.
Figure 9B:
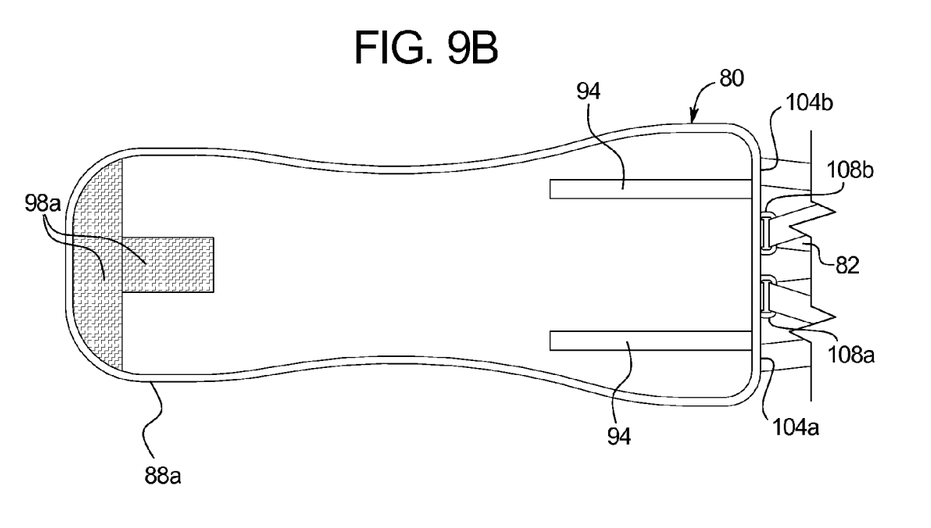

To facilitate utilization of posterior shell 204 with mechanically advantaged belt 80, posterior shell 204 in the illustrated embodiment is adapted with two belt retainer straps 210a, 210b. Each belt retainer strap 210a, 210b is removably installed on posterior shell 204 through upper ports 212a, 212b and lower ports 214a, 214b, respectively, and each belt retainer strap 210a, 210b can have a hook and pile fastener provided thereon. In such manner, at least one end of each belt retainer strap 210a, 210b may be unfastened from posterior shell 204, passed through one of pair of plate attachment straps 94 (FIGS. 9A and 9B) located at the inner posterior surface of belt 80, and then refastened, either to itself or to complementary hook and pile fastener provided on posterior shell 204, thereby securing posterior shell 204 into position proximate belt 80 and defining first posterior configuration 200, or TLSO 202. As illustrated in FIGS. 9A and 9B, plate attachment straps 94 are horizontally long enough to allow general support members or wings 88a and 88b to be tightened or loosened as described above with FIGS. 6A to 6D. The elongation of straps 94 allows wings 88a and 88b to slide or translate relative to posterior shell 204. In one embodiment however, the vertical placement of straps 94 is such that the straps reside near ports 212a, 212b, 214a, and 214b of shell 204, so that the shell is effectively constrained from moving vertically relative to wings 88a and 88b.

In specific embodiments, posterior shell 204 is constructed with a fourteen and one-half (14.5) inch back height, but may alternately be formed as a taller shell 20, with a back height of seventeen and one-half (17.5) inches, wherein utilization as a taller thoracolumbosacral orthosis, or taller TLSO is facilitated.

A second posterior configuration 300 is representatively depicted in FIG. 3A, as a standard chairback brace or lumbosacral orthosis, LSO, 302, tailored for firm support or middle bracing force. LSO 302 includes a posterior shell 304, wherein posterior shell 304 is in once specific embodiment of a fourteen and one-half (14.5) inch height, is of a molded construction, formed from polyethylene or a similarly suited material, and is adapted with interior padding 306, adjustable lordosis 308 and kyphosis 310 straps, and belt retainer straps 311a, 311b. In one embodiment, interior padding 306 is removably secured to posterior shell 304 via hook and pile fastener. FIG. 3B shows the inside of shell 304 with interior padding 306 removed to reveal the hook and pile spots h/p for releasably securing padding 306. To facilitate utilization of posterior shell 304 with mechanically advantaged belt 80, posterior shell 304 is in the illustrated embodiment adapted with two belt retainer straps 311a, 311b.

As representatively depicted in the series of FIGS. 8A to 8D, each belt retainer strap 311a, 311b is in one embodiment removably installed on posterior shell 304 (with interior padding 306 removed) through upper ports 312a, 312b and lower ports 314a, 314b, respectively. Each belt retainer strap 311a, 311b can have hook and pile fastener h/p provided thereon. In such manner, at least one end of each belt retainer strap 311a, 311*b* may be unfastened from posterior shell 304, passed through one of pair of plate attachment straps 94 (FIGS. 9A and 9B) located at the inner posterior surface of belt 80, and then refastened, either to itself or to complementary hook and pile fastener h/p provided on posterior shell 304, thereby securing posterior shell 304 into position proximate belt 80 and defining second posterior configuration 300, or LSO 302.

Figure 8A:
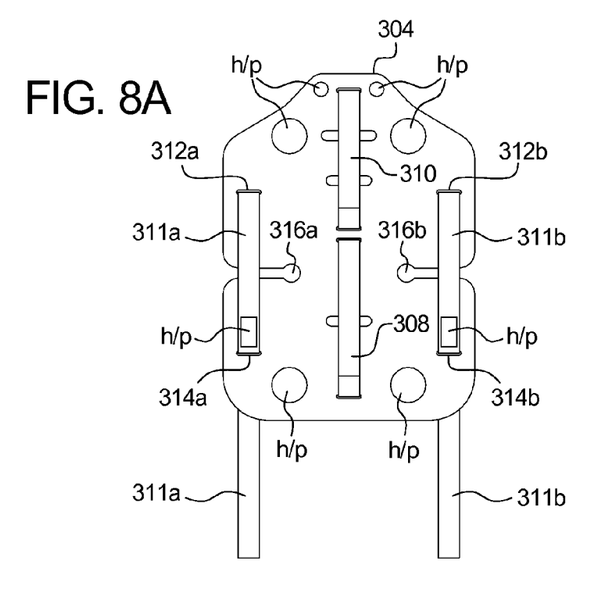
FIGS. 8A to 8D illustrate a series of one embodiment of a posterior shell of the present disclosure being attached to one embodiment of the mechanically advantage belt.
Figure 8B:
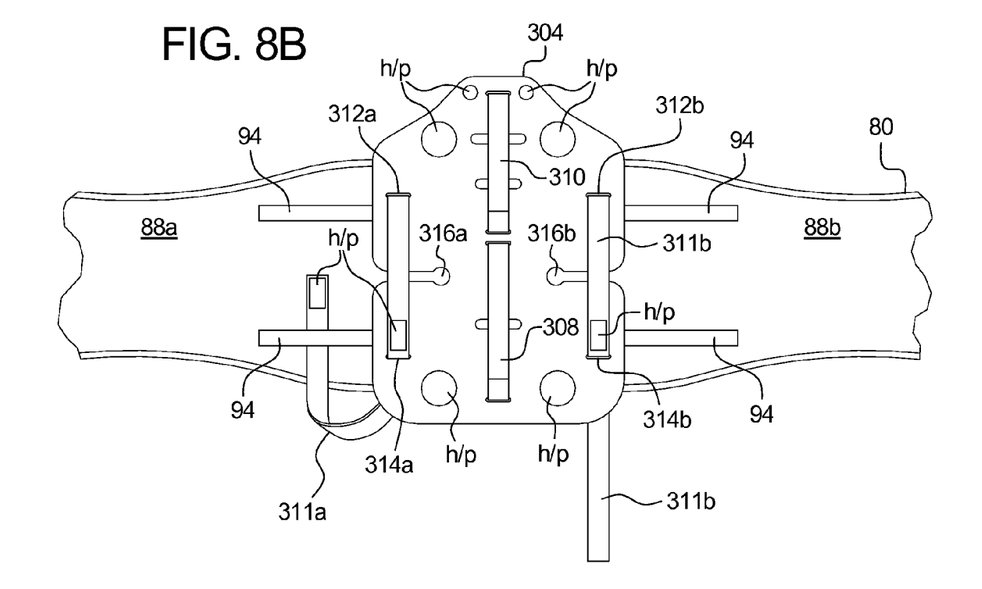
Figure 8C:
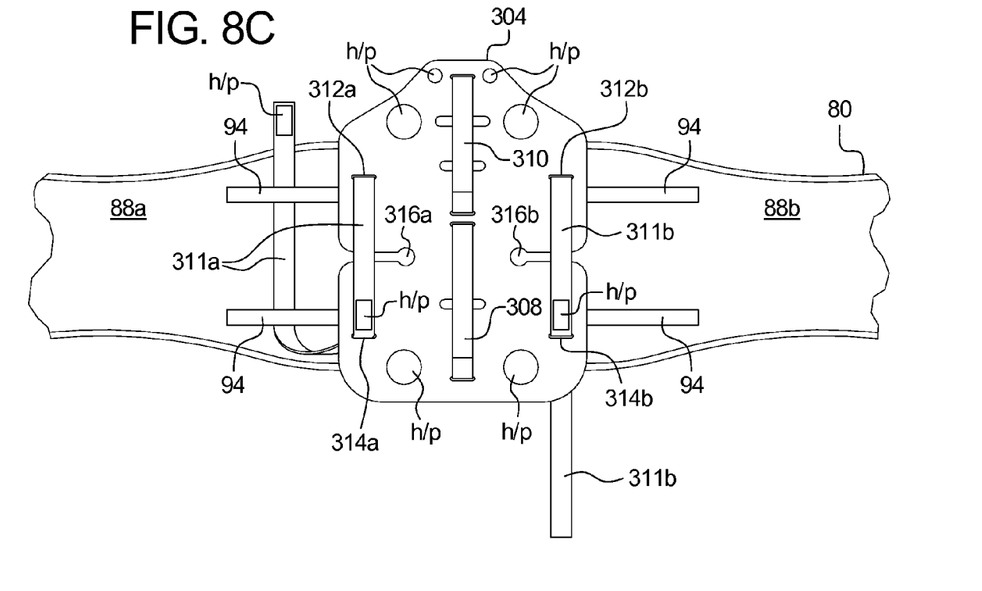
Figure 8D:
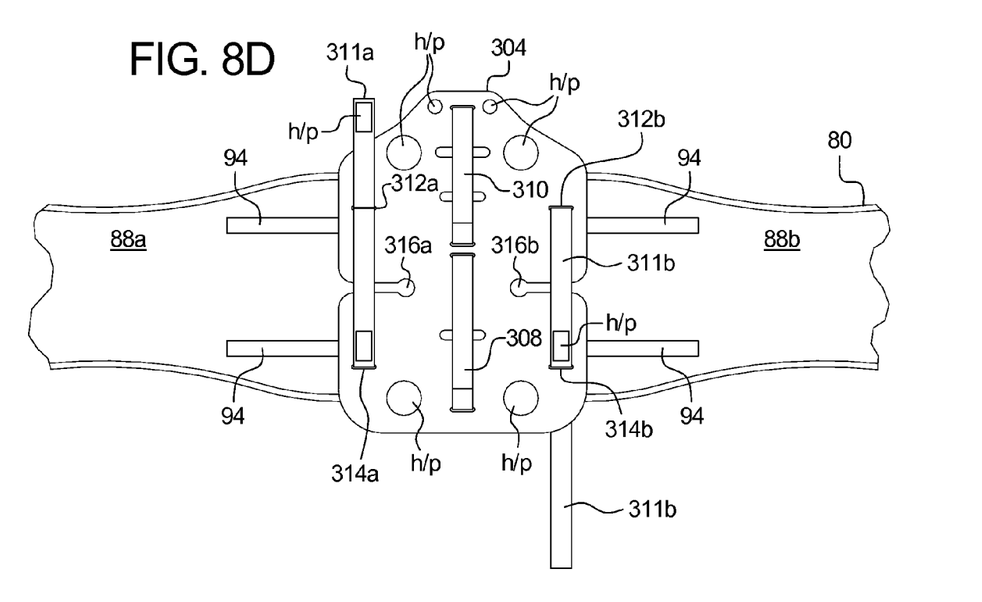

FIGS. 8A to 8D show shell 304 from the inside with inner padding 306 removed from hook and pile fastening spots h/p of shell 304. In FIG. 8A, straps 311*a* and 311*b* extend downwardly from the bottom and on the outside of shell 304. In FIG. 8B, the user has already affixed wing 88*b* to shell 304 via strap 311*b* of shell 304 pulled through attachment straps 94 on the inner surface of wing 88*b*. In FIG. 8B, the user is now pulling strap 311*a* through a lower one of the attachment straps 94 located on the inside surface of wing 88*a*. In FIG. 8C, the user is now threading strap 311*a* of shell 304 through an upper one of the adjustment straps 94 located on the inner surface of wing 88*a*. Wing 88*a* is thereby moveably affixed to shell 304. In FIG. 8D, the user secures the attachment of wing 88*a* to shell 304 by threading strap 311*a* again through upper port 312*a* of shall 304, so that strap 311*a* passes from the outside of shell 304 to the inside of shell 304. On the inside of shell 304, strap 311*a* is secured to itself in the illustrated embodiment, e.g., via hook and pile fasteners h/p. The attachment of wings 88*a* and 88*b* to any of shells 204, 304 and 404 via respective straps 210*a*, 210*b*, 311*a*, 311*b* and 411*a*, 411*b* can be via the structure and methodology just described.

As with first configuration 200 of FIGS. 2A and 2B, and as illustrated in FIGS. 8B to 8D, plate attachment straps 94 are horizontally elongated enough to allow support members or wings 88*a* and 88*b* to be tightened or loosened as described above with FIGS. 6A to 6D. The length of straps 94 allows wings 88*a* and 88*b* to slide or translate relative to posterior shell 304. In one embodiment however, the vertical placement of straps 94 is such that the straps reside near ports 312*a*, 312*b*, 314*a*, and 314*b* so that shell 304 is effectively constrained from moving vertically relative to wings 88*a* and 88*b*.

As illustrated in FIGS. 2A and 2B, aggressive shell 204 is preformed to have a bent contour for aggressive lordosis and lateral support of the user's back, while also providing at least a moderate kyphosis support. As illustrated in FIGS. 3A, 3B, 4A and 4B, on the other hand, respective shells 304 and 404 are provided in a generally flat configuration. Each shell 304 and 404 is however provided with central strapping that allows the user to bend the flattened shells 304 and 404 into a shape similar to that of shell 204, over various degrees from flat to full posterior support.

Figure 7A:
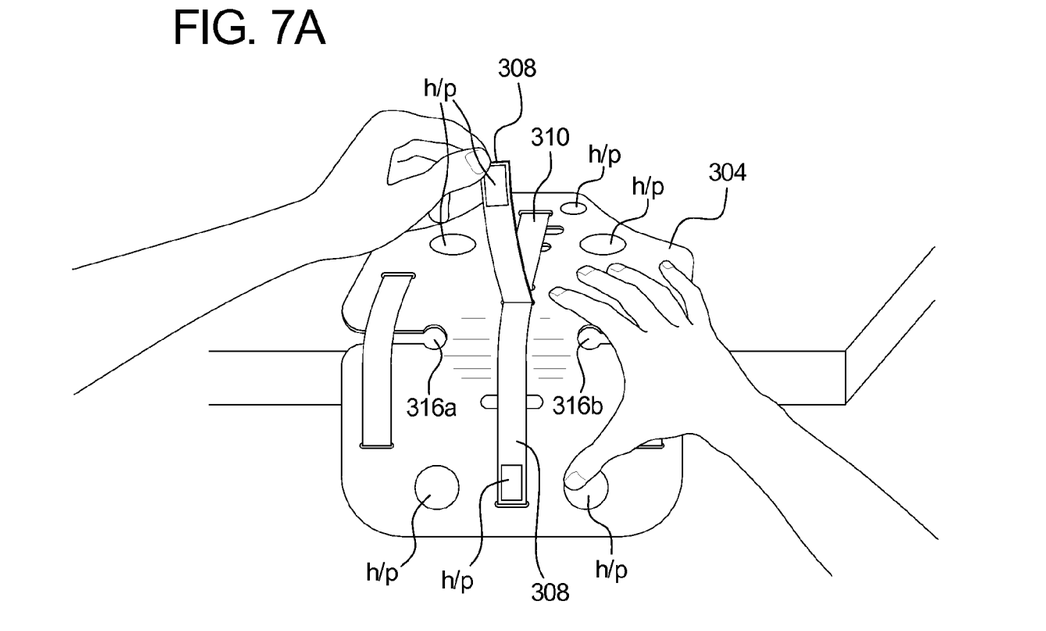
FIGS. 7A to 7D illustrate a pictorial series of one embodiment of the posterior plate of the present disclosure under lordosis and/or kyphosis adjustment.
Figure 7B:
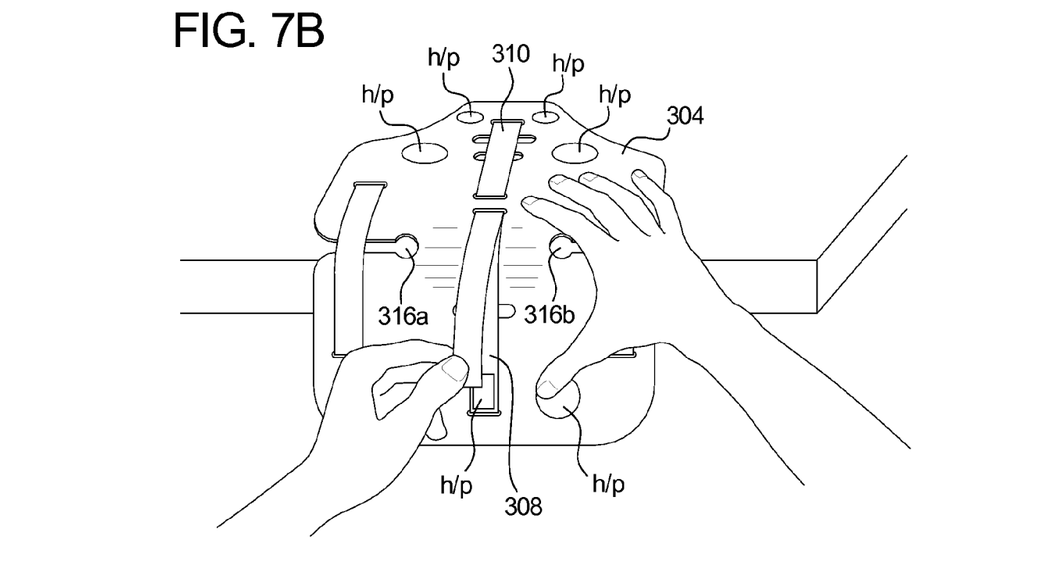

Referring now to the representative series depicted in FIGS. 7A to 7D, as noted, lordosis strap 308 and kyphosis strap 310 may be used for adjustment of posterior shell 304. As illustrated, posterior shell 304 is in one embodiment a sturdy structure, but can be provided with bend accommodating regions 316*a*, 316*b*, and 316*c*, wherein respective adjustable straps 308 and 310 may be selectively tightened to enable maintenance of a selected support-providing bend during wear of orthosis 14. After removal of interior padding 306, e.g., from the hook and pile fasteners h/p on the inside of shell 304, adjustment of lordosis is accomplished in the illustrated embodiment with posterior shell 304 lying over a table edge or the like, with lordosis strap 308 loosened, as depicted in step of FIG. 7A. Posterior shell 304 may be bent to a selected angle or level of deformation, with bending accommodated at regions 316*a*, 316*b*, and lordosis strap 308 may be tightened and re-secured, e.g., via hook and pile fastener h/p, to maintain the selected bend or deformation, as depicted in the step of FIG. 7B. Shell 304 is shown from the inside in FIGS. 7A and 7B, such that the lordosis bend is generally into the page.

Figure 7C:
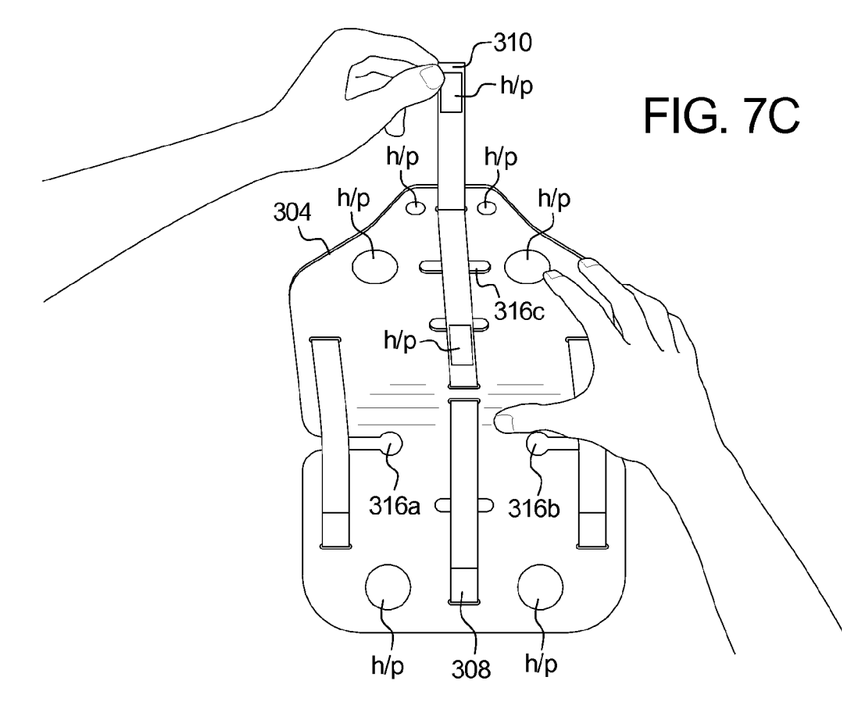
Figure 7D:
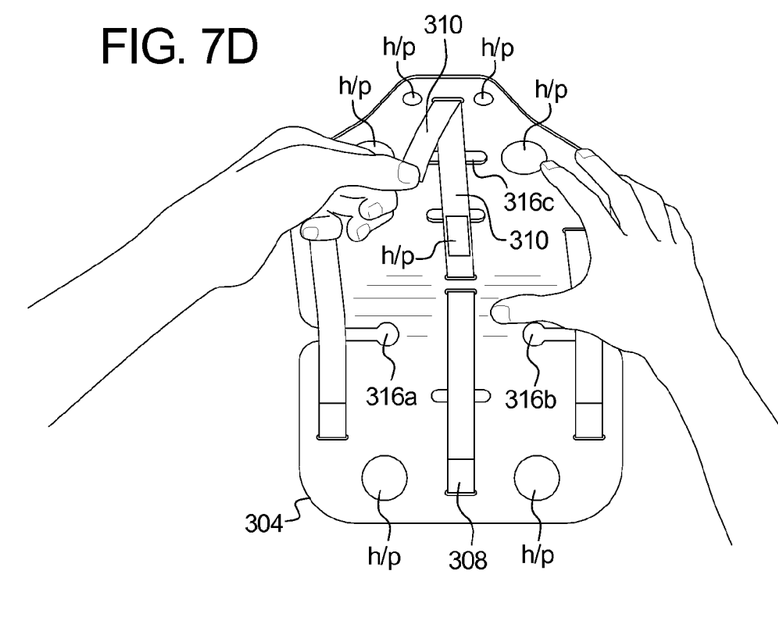

Similarly, adjustment of kyphosis is accomplished in the illustrated embodiment with posterior shell 304 lying on a sturdy surface, with kyphosis strap 310 loosened, as depicted in the step of FIG. 7C. Posterior shell 304 may then be molded or bent to the desired kyphosis deformation, with bending or molding accommodated at region 316*c*, and kyphosis strap 310 may be tightened and re-secured, e.g., via hook and pile fastener h/p, to maintain the selected kyphosis, as depicted in the step FIG. 7D. Shell 304 is shown from the inside in FIGS. 7C and 7D, such that the kyphosis bend is generally out of the page.

A third posterior configuration 400 is representatively depicted in FIGS. 4A and 4B, as mid-lumbosacral orthosis, mid-LSO, 402, tailored for moderate or lower support or bracing force. Mid-LSO 402 in the illustrated embodiment includes a posterior shell 404, wherein posterior shell 404 in once specific embodiment is of a ten and one-half (10.5) inch height, is of molded construction, e.g., formed from polyethylene or a similarly suited material, and is adapted with interior padding 406, an adjustable lordosis 408 strap, and belt retainer straps 411*a*, 411*b*. In one embodiment, interior padding 406 is removably secured to posterior shell 404 via hook and pile fastener. FIG. 4B is shown from the inside with interior padding 406 removed, revealing hook and pile fastening spots h/p on the inside surface of shell 304 for securing padding 406.

To facilitate utilization of posterior shell 404 with mechanically advantaged belt 80, posterior shell 404 like above is provided with two belt retainer straps 411*a*, 411*b*. Each belt retainer strap 411*a*, 411*b* is, like above, removably installed on posterior shell 404 (with interior padding 406 removed) through upper ports 412*a*, 412*b* and lower ports 414*a*, 414*b*, respectively. Each belt retainer strap 411*a*, 411*b* in one embodiment has hook and pile fasteners h/p provided thereon. In such manner, at least one end of each belt retainer strap 411*a*, 411*b* may be unfastened from posterior shell 404, passed through one of pair of plate attachment straps 94 (FIGS. 9A and 9B) located at the inner posterior surface of belt 80, and then refastened, either to itself or to complementary hook and pile fastener h/p provided on posterior shell 404, thereby securing posterior shell 404 into position proximate belt 80 and defining third posterior configuration 400, or mid-LSO 402.

As illustrated in FIGS. 9A and 9B, plate attachment straps 94 are horizontally elongated enough to allow enough support members or wings 88*a* and 88*b* to be tightened or loosened as described above with FIGS. 6A to 6D. The length of straps 94 allows wings 88*a* and 88*b* to slide or translate relative to posterior shell 404. In one embodiment however, the vertical placement of straps 94 is such that the straps reside near ports 412*a*, 412*b*, 414*a*, and 414*b* so that shell 404 is effectively constrained from moving vertically relative to wings 88*a* and 88*b*.

Because shell 404 is shorter than shell 304, shell 404 may be provided with only a single central strap for selectively bending the initially flat shell 404 into a shape providing for more aggressive posterior support. Similar to LSO 302, for mid-LOS 402, lordosis strap 408 may be used for adjustment of posterior shell 404. Posterior shell 404 can be a sturdy structure, but with bend accommodating regions 416*a*, 416*b* provided, wherein adjustable strap 408 may be selectively tightened to enable maintenance of a selected bend or deformation during use with posterior configuration 400. After removal of interior padding 406, adjustment of lordosis can be accomplished with posterior shell 404 lying over a table edge or the like, with lordosis strap 408 loosened. Posterior shell 404 may be bent to a selected angle or deformation, with bending accommodated at regions 416a, 416b, after which lordosis strap 408 may be tightened and re-secured, e.g., via hook and pile fastener h/p, to maintain the selected bend or deformation.

Pocket 98b of belt 80 (FIG. 9A), for any of the posterior shell embodiments described herein, may be used for selective addition of an anterior panel (not illustrated) to any posterior configuration. Addition of an anterior panel is particularly useful with mid-LSO 402 of third posterior configuration 400. It is expressly contemplated to provide a multistage bracing therapy that varies any combination of (i) the varying back support providing posterior shells and (ii) the use or not of a complimentary anterior panel The most aggressive therapy uses the most aggressive posterior shell and an anterior plate. The least aggressive therapy uses no posterior shell and no anterior panel. In between could be, for example, (a) a staged reduction of posterior shell aggressiveness used with no use of anterior panel, (b) a staged reduction of posterior shell aggressiveness with use in each stage of an anterior panel, (c) a staged reduction of posterior shell aggressiveness with use in alternating stages of an anterior panel, (d) a staged reduction of posterior shell aggressiveness with an anterior panel used at all times with certain posterior shells and at no time with other posterior shells, or (e) a staged reduction of posterior shell aggressiveness with an anterior panel used at only certain times with certain posterior shells and at no time with other posterior shells. Other combinations would be within the scope of the invention, for example, a therapy does not require that all of the posterior shells or even that multiple ones of the shells described herein be used.

Having thus described exemplary embodiments of the present apparatus and method, it should be noted by those skilled in the art that the within disclosures are exemplary only, and that various other alternatives, adaptations, and modifications may be made within the scope of the present disclosure. Accordingly, the present disclosure is not limited to the specific embodiments illustrated herein, but is limited only by the following claims.

The invention is claimed as follows:

1. A mechanically advantaged spinal system comprising:
   a belt including a mechanically advantaged closure mechanism; and
   a plurality of interchangeable shells, each of the plurality of interchangeable shell constructed and arranged (i) for selective and individual carriage by the belt and (ii) to provide a different level of bracing force compared to each of the other interchangeable shell.

2. The spinal system of claim 1, wherein at least one of the plurality of shells further includes a lordosis adjustment feature.

3. The spinal system of claim 2, wherein the lordosis adjustment feature includes a strap structured and arranged to bias the corresponding shell.

4. The spinal system of claim 3, wherein the lordosis adjustment strap is a first strap, and which includes at least one additional strap for connecting the belt to the shells individually.

5. The spinal system of claim 3, wherein the strap is structured and arranged to adjustably attach to itself.

6. The spinal system of claim 1, wherein at least one of the plurality of shells further includes a kyphosis adjustment feature.

7. The spinal system of claim 6, wherein the kyphosis adjustment feature includes a strap structured and arranged to bias the corresponding shell.

8. The spinal system of claim 7, wherein the kyphosis adjustment strap is a first strap, and which includes at least one additional strap for connecting the belt to the shells individually.

9. The spinal system of claim 7, wherein the strap is structured and arranged to adjustably attach to itself.

10. The spinal system of claim 1, wherein at least one of the shells includes a lordosis adjustment feature and a kyphosis adjustment feature.

11. The spinal system of claim 1, wherein the mechanically advantaged closure mechanism provides at least a 6:1 mechanical advantage.

12. The spinal system of claim 1, wherein at least one of the shells is pre-formed to provide the bracing force.

13. The spinal system of claim 1, wherein the belt includes first and second wings releasably attachable to each other and a clinching strap as part of and for operating the mechanically advantaged closure system.

14. The spinal system of claim 13, wherein the mechanically advantaged closure system further includes a member connected to adjacent ends of the first and second wings, the clinching strap pulling the member to tighten the belt.

15. The spinal system of claim 14, wherein the member is a strap in looped communication with the adjacent ends of the first and second wings.

16. The spinal system of claim 1, which includes an anterior support panel carried by the belt.

17. A mechanically advantaged spinal method comprising:
   bracing a patient at a beginning of a treatment by allowing the patient to attach a first bracing shell, structured and arranged to provide a largest bracing force, to a belt and allowing the patient to selectively tighten the belt using mechanical advantage;
   bracing the patient at an intermediate point of treatment by allowing the patient to attach a second bracing shell, structured and arranged to provide an intermediate bracing force, to the belt and allowing the patient to selectively tighten the belt using mechanical advantage; and
   bracing the patient at an end of treatment by allowing the patient to attach a third bracing shell, structured and arranged to provide a lower bracing force, to the belt and allowing the patient to selectively tighten the belt using mechanical advantage.

18. The mechanically advantaged spinal method of claim 17, wherein providing at least one of the intermediate and lower bracing forces includes adjustably applying the at least one of the intermediate and the lower bracing forces.

19. The mechanically advantaged spinal method of claim 17, which includes attaching the first, second and third bracing shells in at least a substantially same manner.

20. The mechanically advantaged spinal method of claim 17, which includes providing the mechanical advantage at the beginning, intermediate point and end of treatment in at least a substantially same manner.

\* \* \* \* \*